United States Patent [19]

Nugent et al.

[11] Patent Number: 5,397,774
[45] Date of Patent: Mar. 14, 1995

[54] PYRAZOLOPYRIMIDINE AND PYRIMIDINYL BISPHOSPHONIC ESTERS AS ANTI-INFLAMMATORIES

[75] Inventors: Richard A. Nugent, Galesburg; Stephen T. Schlachter, Kalamazoo, both of Mich.

[73] Assignee: The Upjohn Company, Kalamazoo, Mich.

[21] Appl. No.: 175,216

[22] Filed: Dec. 28, 1993

Related U.S. Application Data

[63] Continuation-in-part of Ser. No. 725,047, Jul. 3, 1991, abandoned, and a continuation-in-part of Ser. No. 725,046, Jul. 3, 1991, abandoned.

[51] Int. Cl.$^6$ .................. A61K 31/675; C07F 9/6512; C07F 9/6574; C07F 9/6561
[52] U.S. Cl. ........................................ 514/81; 514/86; 544/243; 544/244; 544/281
[58] Field of Search ............................ 544/244; 514/81

[56] References Cited

U.S. PATENT DOCUMENTS

| | | | |
|---|---|---|---|
| 3,683,080 | 8/1972 | Francis | 514/108 |
| 4,746,654 | 5/1988 | Breliere et al. | 514/108 |
| 4,777,163 | 10/1988 | Bosies et al. | 514/80 |
| 4,871,720 | 10/1989 | Jaeggi | 544/243 |
| 5,071,840 | 12/1991 | Ebetino et al. | 544/243 |

FOREIGN PATENT DOCUMENTS

| | | |
|---|---|---|
| 51534/85 | 12/1985 | Australia . |
| 354806A2 | 2/1990 | European Pat. Off. . |
| A-2703712 | 8/1978 | Germany . |
| 3626058A1 | 2/1988 | Germany . |
| 3719513-A | 12/1988 | Germany . |

OTHER PUBLICATIONS

Nugent et al, *Chemical Abstracts*, vol. 118, No. 255 119 (1993) (Abstract for EP 521622).

Nugent et al American Chemical Society spring meeting on Jun. 9, 1988, PD 7244-88-021.
Sietsema et al Chemical Abstracts No. 191396, vol. 112, No. 21, May 21, 1990.
Sietsema et al Drug Exp. Clin. Res., vol. 15, No. 9, pp. 389-396, 1989.

*Primary Examiner*—Emily Bernhardt
*Attorney, Agent, or Firm*—Donald Corneglio

[57] ABSTRACT

Compounds useful in the treatment of inflammation structurally represented as

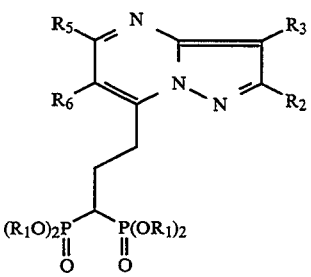

FORMULA 1;

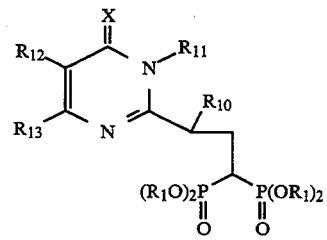

FORMULA 2;

wherein X is O or S and the R groups are as herein defined. The compounds are useful as anti-inflammatory and anti-arthritic agents without inhibiting prostaglandin synthesis.

9 Claims, No Drawings

PYRAZOLOPYRIMIDINE AND PYRIMIDINYL BISPHOSPHONIC ESTERS AS ANTI-INFLAMMATORIES

CROSS-REFERENCE TO RELATED APPLICATIONS

This application is a continuation of International Patent Application No. PCT/US92/05398, filed 1 Jul. 1992; which is a continuation-in-part of U.S. Ser. Nos. 07/725,047 and 07/725,046, both filed 3 Jul. 1991, and both now abandoned.

BACKGROUND OF THE INVENTION

The present invention is directed toward pyrazolopyrimidine (Formula 1) and pyrimidinyl (Formula 2) bisphosphonic esters, acids, and their pharmaceutically acceptable salts which are useful as anti-inflammatories and anti-arthritic agents.

The present compounds, unlike other anti-inflammatory agents, are not prostaglandin synthetase inhibitors. Typically, prostaglandin synthetase activity is inhibited by nonsteroidal anti-inflammatory agents and many of their actions, including side effects, have been attributed to this inhibition of prostaglandin synthesis. The subject compounds still possess anti-inflammatory response without suppressing the production of prostaglandin. This can be an advantage because it is known that at high concentrations prostaglandins are considered anti-inflammatory. The subject compounds are also useful for treating arthritis and its related symptoms such as inflammation and prevention of excessive bone regrowth and remodeling.

DESCRIPTION OF THE RELATED ART

U.S. Pat. No. 4,746,654 discloses bisphosphonates useful as anti-inflammatory agents.

Australian Patent A-51534/85 discloses bisphosphonates useful in treating abnormal calcium and phosphorous metabolism and useful in treating arthritis.

U.S. Pat. No. 3,683,080 discloses polyphosphonates, in particular diphosphonates useful in inhibiting anomalous deposition and mobilization of calcium phosphate in animal tissue.

DE 3,719,513-A (Derwent 89-000580/01) discloses diphosphonic acid derivatives useful in treatment of disorders of calcium metabolism.

With respect to Formula 1 compounds, the alkylation of 5,7-dimethyl pyrazolo[1,5-a]pyrimidines was disclosed at the American Chemical Society spring meeting on Jun. 9, 1988, PD 7244-88-021.

Yamanouchi has published imidazo[1,2-a]pyridines and imidazo[1,2-a]imidazoles (EP 354-806 A2, Feb. 14, 1990). Boehringer Mannheim DE 3626-058 A1 discloses heteroaromatic diphosphonates bound to a diphosphonate.

SUMMARY OF THE INVENTION

In one aspect, the subject invention consists of pyrazolopyrimidine (Formula 1) and pyrimidinyl (Formula 2) bisphosphonic esters, acids, and their pharmaceutically acceptable salts, which are structurally represented as:

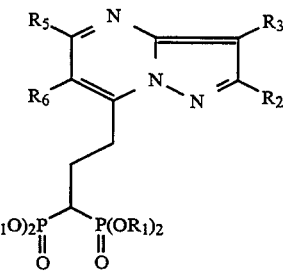

FORMULA 1;

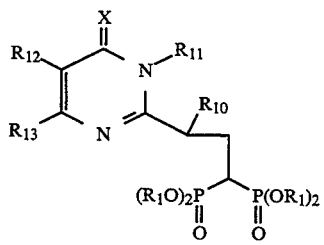

FORMULA 2;

wherein X is O or S;

each $R_1$ is the same or different and is selected from the group consisting of H, Na, K, tromethamine, $C_1$-$C_6$ alkyl, $CH_2$-phenyl, phenyl (optionally substituted with 1 to 5 $NO_2$, halo, or $C_1$-$C_4$ alkyl), or both $OR_1$ on the same P are taken together along with $CH_2$—$CH_2$, $CH_2$—$CH_2$—$CH_2$, or $CH_2$—$C(CH_3)_2$—$CH_2$ to form a heterocyclic ring having one P, two O and two or three carbon atoms;

$R_2$ is hydrogen, $C_1$-$C_6$ alkyl, benzoyloxy, benzyloxy, $C_1$-$C_6$ alkoxy, phenoxy, $C_3$-$C_7$ cycloalkyl, phenyl (optionally substituted with 1 or 2 phenyls, or 1 to 5 halo, $NO_2$, CN, $CF_3$, $C_1$-$C_{10}$ alkyl, $C_3$-$C_7$ cycloalkyl, $C_1$-$C_6$ alkoxy or $C_1$-$C_6$ alkylthio), 2-, 4- or 5-pyrimidyl (optionally substituted with 1 or 2 phenyls, or 1 to 3 halo, $NO_2$, CN, $CF_3$, $C_1$-$C_{10}$ alkyl, $C_3$-$C_7$ cycloalkyl, $C_3$-$C_7$ alkoxy, or $C_1$-$C_6$ alkylthio), 2-, 3- or 4-pyridyl (optionally substituted with 1 or 2 phenyls, or 1 to 4 halo, $NO_2$, CN, $CF_3$, $C_1$-$C_{10}$ alkyl, $C_3$-$C_7$ cycloalkyl, $C_1$-$C_6$ alkoxy or $C_1$-$C_6$ alkylthio), 1- or 2- naphthalenyl (optionally substituted with 1 or 2 phenyls, or 1 to 7 halo, $NO_2$, CN, $CF_3$, $C_1$-$C_{10}$ alkyl, $C_3$-$C_7$ cycloalkyl, $C_1$-$C_6$ alkoxy or $C_1$-$C_6$ alkylthio);

$R_3$ is H, CN, $CO_2R_1$, $COR_2$, $CON(R_5)_2$, halo, $NO_2$, CN, $CF_3$, $C_1$-$C_{10}$ alkyl, $C_3$-$C_7$ cycloalkyl, or phenyl;

$R_5$ is H, $C_1$-$C_6$ alkyl or $C_3$-$C_7$ cycloalkyl;

$R_6$ is H, halo, or $C_1$-$C_6$ alkyl;

$R_{10}$ is H, $C_1$-$C_6$ alkyl, $C_3$-$C_7$ cycloalkyl, or phenyl (optionally substituted with 1 or 2 phenyls, or 1 to 5 halos, $NO_2$, CN, $CF_3$, $C_1$-$C_{10}$ alkyl, $C_3$-$C_7$ cycloalkyl, $C_1$-$C_6$ alkoxy or $C_1$-$C_6$ alkylthio;

$R_{11}$ is H, $C_1$-$C_6$ alkyl, $C_3$-$C_7$ cycloalkyl, allyl, $CH_2OR_{14}$, $CH_2$-phenyl, or phenyl (optionally substituted with 1 to 5 $NO_2$, halos, or $C_1$-$C_4$ alkyl);

$R_{12}$ is H, $C_1$-$C_6$ alkyl, halo, $NO_2$;

$R_{13}$ is hydrogen, $C_1$-$C_6$ alkyl, $C_3$-$C_7$ cycloalkyl, or phenyl (optionally substituted with 1 to 2 phenyls, or 1 to 5 halos, $NO_2$, CN, $CF_3$, $C_1$-$C_{10}$ alkyl, $C_3$-$C_7$ cycloalkyl, $C_1$-$C_6$ alkoxy or $C_1$-$C_6$ alkylthio), 2-, 3- or 4-pyridyl (optionally substituted with 1 to 2 phenyls, or 1 to 4 halos, $NO_2$, CN, $CF_3$, $C_1$-$C_{10}$ alkyl, $C_3$-$C_7$ cycloalkyl, $C_1$-$C_6$ alkoxy or $C_1$-$C_6$ alkylthio), 1- or 2-naphthalenyl (optionally substituted with 1 to 2 phenyls, or 1 to 7 halos, $NO_2$, CN, $CF_3$, $C_1$-$C_{10}$ alkyl, $C_3$-$C_7$ cycloalkyl, $C_1$-$C_6$ alkoxy or $C_1$-$C_6$ alkylthio), piperidine, morpholine, pyrrolidine, $N(R_5)_2$, $NHC(O)R_{14}$, $NHC(O)OR_{14}$ or $R_{12}$ and $R_{13}$ form a ring of 4 to 7 members (core atoms in the ring) having 4 to 7 carbons, 1 to 3 nitrogens, 0 to 2 oxygens, and 0 to 2 sulfurs; and $R_{14}$ is $C_1$-$C_6$ alkyl, $C_3$-$C_7$ cycloalkyl, allyl, $CH_2$-phenyl, or phenyl (optionally substituted with 1 to 5 $NO_2$, halos, or $C_1$-$C_4$ alkyl).

In another aspect, the present invention comprises the use of these compounds in humans and lower animals as a safe and effective treatment of diseases characterized by abnormal phosphate and calcium metabolism, and as a treatment of inflammation. These diseases include osteoporosis, Paget's disease, periodontal disease, rheumatoid arthritis, osteoarthritis, neuritis, bursitis, soft tissue mineralization disorders, ankylosing spondylitis, atherosclerosis, multiple myeloma of bone, metastic bone disease, and mitral valve calcification. These compounds do not inhibit cyclooxygenase or lipoxygenase metabolism of arachidonic acid and so constitute a novel method of treating inflammation.

A method for treating inflammation comprises administering to an animal in need of such treatment an anti-inflammatory effective amount of a compound of Formula 1 or 2. Routes of administration include oral, intramuscular, intravenous, transdermal, intra-articular, subcutaneous, or intraperitoneal. An effective amount is an amount whereby the symptoms of inflammation or arthritis such as pain and discomfort are relieved or reduced or mobility of the affected area is increased. A typical dosage is about 0.001 mg to 1.0 gram with dose determined by the particular mode of administration, use and frequency of administration.

DETAILED DESCRIPTION OF THE INVENTION

The present invention comprises pyrazolopyrimidine (Formula 1) and pyrimidinyl (Formula 2) bisphosphonic esters, acids, and their pharmaceutically acceptable salts, which are structurally represented by Formula 1 and 2. The compounds are particularly useful in the treatment of arthritis and its associated symptoms such as inflammation and excessive bone growth or remodeling. In Formulas 1 and 2, the variable designations are further defined as follows.

The carbon content of various hydrocarbon containing moieties is indicated by a prefix designating the minimum and maximum number of carbon atoms in the moiety, i.e., the prefix $C_i$-$C_j$ defines the number of carbon atoms present from the integer "i" to the integer "j" inclusive. Thus, $C_1$-$C_3$ alkyl refers to alkyl of 1-3 carbon atoms, inclusive, or methyl, ethyl, propyl, and isopropyl.

With respect to the above, $C_1$-$C_6$ alkyl is methyl, ethyl, propyl, butyl, pentyl, hexyl, and isomeric forms thereof. $C_3$-$C_7$ cycloalkyl is cyclopropane, cyclobutane, cyclopentane, cyclohexane, cycloheptane and isomeric forms thereof.

The term "halo" includes fluoro, chloro, bromo and iodo.

$C_1$-$C_8$ alkylthio are methylthio, ethylthio, propylthio, butylthio, pentylthio, hexylthio, heptylthio, octothio, and isomeric forms thereof.

$C_1$-$C_8$ alkoxy are methoxy, ethoxy, propoxy, butoxy, pentoxy, hexoxy, heptoxy, octooxy, and isomeric forms thereof.

Pharmaceutically acceptable salts means salts useful for administering the compounds of this invention and include hydrochloride, hydrobromide, hydroiodide, sulfate, phosphate, acetate, propionate, lactate, mesylate, maleate, malonate, succinate, tartrate, citric acid and the like. These salts may be in hydrated form.

The pyrazolopyrimidine bisphosphonic esters, acids and derivatives (Formula 1) useful as anti-inflammatories and antiarthritics are prepared as shown in Examples 1–13 (Compounds a–o). The general pyrazolopyrimidine heterocyclic ring structure can be prepared by procedures well known in the art. For example, the synthesis of pyrazolo[1,5-a]pyrimidines is described by M. H. Elnagdi, G. E. H. Elgemeie, and M. R. H. Elmoghayar in Advances in Heterocyclic Chemistry, Vol. 41, pg 319; M. R. H. Elmoghayar et al., Pyrimidine Derivatives and Related Compounds, Arch. Pharm. (Weinheim), 316, pp 697–702 (1983); and T. Novinson et al., 3-Substituted 5,7-Dimethylpyrazolo(1,5-a)pyrimidines, J. Med. Chem., 17, pp 645–48 (1974).

One procedure for synthesizing the Formula 1 compounds of this invention is by dissolving the pyrazolopyrimidine in a suitable solvent (THF, pyridine or a combination of the two). This liquid is added dropwise to a $-78°$ C. THF solution, although this can also be done at $0°$ C., of a strong kinetic base (lithium hexamethyldisilazide or lithium diisopropyl amide) and the resulting solution is stirred for about 30 minutes at $-78°$ C., although this can also be done at $0°$ C. Vinylidene diphosphonate is added either neat or in THF solution to the cold reaction, whereupon the reaction is allowed to warm to ambient temperature. Specific workup conditions are described in the examples.

The synthesis of the corresponding Formula 1 acid is accomplished by either of two procedures, both of which are well known to those skilled in the art. The first is to reflux the tetraester in concentrated hydrochloric acid for 12 hours and concentrate the solution, and is illustrated by the synthesis of Compound "b" from "a" of Example 1, below. Alternatively, one can treat the tetraester with trimethylsilyl bromide followed by aqueous workup to isolate the acid. The Formula 1 compounds of this group are fluorescent and as such allow for the tracing of the compound through biological tissue.

The Formula 1 compounds of this invention have been tested in a Delayed Type Hypersensitivity Granuloma Assay (DTH GRA) model for inflammation. This assay is described by Dunn, C. J. et al., "Development of a delayed-type hypersensitivity granuloma model in the mouse for the study of chronic immune-mediated inflammatory disease," Agents and Actions, 27, 3/4 (1989) and "Murine Delayed-Type Hypersensitivity Granuloma," Int. J. Immunopharmc., 12, 8, 899–904 (1990).

Briefly, mBSA-sensitized mice have a DTH granuloma (DTH GRA) lesion induced by subcutaneously implanting a mBSA-soaked filter which is excised after nine days. Compounds are administered to the mice to determine their effect on the lesions. The results are recorded as percent inhibition. The larger the inhibition, the more effective the compound. Inhibition of 10 to 20% is considered to indicate anti-granuloma activity. Greater than 30% inhibition is good activity.

The DTH GRA data obtained from the compounds of Formula 1 are shown in Table 1. The compounds are scored as having anti-inflammatory activity at 10–20% inhibition and good activity at greater than 30% inhibition.

The "compound designations" correspond to the Examples' designations. The particular compounds designated are as follows a) (3-(3-Cyano-2,5-dimethyl-pyrazolo(1,5-a)pyrimidin-7-yl)propylidene)bisphosphonic acid tetraethyl ester,
c) (3-(3-Cyano-5-methyl-2-phenyl-pyrazolo(1,5-a)pyrimidin-7-yl)-propylidene)bisphosphonic acid tetraethyl ester,
d) (3-(3-Bromo-2,5-dimethyl-pyrazolo(1,5-a)pyrimidin-7-yl)-propylidene)bisphosphonic acid tetraethyl ester,
e) (3-(3-Nitro-2,5-dimethyl-pyrazolo(1,5-a)pyrimidin-7-yl)-propylidene)bisphosphonic acid tetraethyl ester,
f) (3-(2-Benzoyloxy-5-methyl-pyrazolo(1,5-a)pyrimidin-7-yl)-propylidene)bisphosphonic acid tetraethyl ester,
g) (3-(2-Benzyloxy-5-methyl-pyrazolo(1,5-a)pyrimidin-7-yl)-propylidene)bisphosphonic acid tetraethyl ester,
h) (3-(2-Hexyloxy-5-methyl-pyrazolo(1,5-a)pyrimidin-7-yl)propylidene)-bisphosphonic acid tetraethyl ester,
i) (3-(5-Methyl-2-phenyl-pyrazolo(1,5-a)pyrimidin-7-yl)-propylidene)bisphosphonic acid tetraethyl ester,
j) (3-(3-Iodo-5-methyl-2-phenyl-pyrazolo(1,5-a)pyrimidin-7-yl)-propylidene)bisphosphonic acid tetraethyl ester,
k) (3-(3-Chloro-5-methyl-2-phenyl-pyrazolo(1,5-a)pyrimidin-7-yl)-propylidene)bisphosphonic acid tetraethyl ester,
l) (3-(3-Bromo-5-methyl-2-phenyl-pyrazolo(1,5-a)pyrimidin-7-yl)-propylidene)bisphosphonic acid tetraethyl ester,
m) (3-(3-Cyano-2,5-dimethyl-pyrazolo(1,5-a)pyrimidin-7-yl)-propylidene)bisphosphonic acid tetramethyl ester
n) (3-(3-Cyano-2,5-dimethyl-pyrazolo(1,5-a)pyrimidin-7-yl)-propylidene)bis(5,5-dimethyl-2,2'-dioxide-1,3,2-dioxaphosphorinane) and
o) (3-(6-Chloro-3-cyano-2,5-dimethyl-pyrazolo(1,5 -a)-pyrimidin-7-yl)-propylidene)bisphosphonic acid tetraethyl ester.

TABLE 1

| Compound Designation | % Inhibition (10 mg/kg) PO |
|---|---|
| a | 46 |
| c | 26 |
| d | 44 |
| e | 41 |
| f | 41 |
| g | 44 |
| h | 49 |
| i | 47 |
| j | 53 |
| k | 31[a] |
| l | 23[a] |
| m | 41 |
| n | 45 |
| o | 53 |

[a]Tested at 50 mg/kg

The pyrimidinyl bisphosphonic esters, acids and derivatives (Formula 2) useful as an anti-inflammatory and antiarthritic are prepared as shown in Examples 14 through 17 (Compounds "p-ss"). The synthesis of 4-pyrimidinones is well known to those skilled in the art. Briefly, a β-keto ester is treated with acetamidine hydrochloride in the presence of base to form the parent heterocycle. The base can be sodium hydroxide, potassium carbonate, sodium methoxide, or sodium ethoxide. The reaction can be run neat or the solvent can be ethanol or methanol. N-alkylated derivatives are synthesized by treatment of the parent compound with an electrophile in the presence of base, such as potassium carbonate, sodium hydride, or potassium fluoride.

In one procedure, the Formula 2 compounds can be synthesized by reacting the alkylated pyrimidinones with a strong base, such as lithium hexamethyl disilazide or lithium diisopropyl amide, then treatment with a diphosphonate vinylidene such as ethenylidenebis-tetraethyl ester phosphonic acid or 2,2'-Ethenylidene bis(5,5-dimethyl-2,2'-dioxide-1,3,2-dioxaphosphorinane). Compounds are purified either by chromatography or crystallization.

The Formula 2 compounds have been tested by the Delayed Type Hypersensitivity Granuloma (DTH GRA) model for inflammation as explained above. Again, as in Table 1, the results are recorded as percent inhibition. The larger the inhibition, the more effective the compound. Inhibition of 10 to 20% is considered to indicate anti-granuloma activity. Greater than 30% inhibition is good activity.

The DTH GRA data obtained from the compounds of Formula 2 are shown in Table 2. The "compound designations" correspond to the Examples' designations in Examples 14–17. The compound names are as follows:

p) (3-(2-(3-Methyl-4-oxo-6-phenyl-4(3H)-pyrimidinyl))-propylidine)bisphosphonic acid tetraethyl ester,
q) (3-(2-(3-Methyl-4-oxo-6-phenyl-4(3H)-pyrimidinyl))-propylidine)bisphosphonic acid disodium salt,
r) (3-(2-(3-Benzyl-4-oxo-6-phenyl-4(3H)-pyrimidinyl))-propylidine)bisphosphonic acid tetraethyl ester,
s) (3-(2-(3-Methyl-4-oxo-6-(3-fluoro-phenyl)-4(3H)-pyrimidinyl))-propylidine)bisphosphonic acid tetraethyl ester,
t) (3-(2-(3-Allyl-4-oxo-6-phenyl-4(3H)-pyrimidinyl))-propylidine)bisphosphonic acid tetraethyl ester,
v) (3 -(2-(3-Methyl-4-oxo-6-(3 -methyl-phenyl)-4(3H)-pyrimidinyl))-propylidine)bisphosphonic acid tetraethyl ester,
w) (3-(2-(3-Methyl-4-oxo-6-(3-methoxy-phenyl)-4(3H)-pyrimidinyl))-propylidine) bisphosphonic acid tetraethyl ester,
x) (3-(2-(3-Methyl-4-oxo-6-(3-trifluoromethyl-phenyl)-4(3H)-pyrimidinyl))propylidine)bisphosphonic acid tetraethyl ester,
y) (3-(2-(3-Methyl-4-oxo-5-bromo-6-phenyl-4(3H)-pyrimidinyl))-propylidine)bisphosphonic acid tetraethyl ester,
z) (3-(2-(3-Methyl-4-oxo-6-phenyl-4(3H)-pyrimidinyl))-propylidine)bisphosphonic acid tetramethyl ester,
aa) (3-(2-(3-Methyl-4-oxo-6-(4-bromophenyl)-4(3H)-pyrimidinyl))-propylidine)bisphosphonic acid tetraethyl ester,
bb) (3-(2-(3-Methyl-4-oxo-6-(4-methoxyphenyl)-4(3H)-pyrimidinyl))-propylidine)bisphosphonic acid tetraethyl ester,
cc) (3-(2-(3-Methyl-4-oxo-6-(4-dimethylaminophenyl)-4(3H)-pyrimidinyl))-propylidine)bisphosphonic acid tetraethyl ester,
ee) (3-(2-(3-Methyl-4-oxo-6-(4-ethoxyphenyl)-4(3H)-pyrimidinyl))-propylidine)bisphosphonic acid tetraethyl ester,
gg) (3-(2-(3-Benzyl-4-oxo-6-phenyl-4(3H)-pyrimidinyl))-propylidine)bisphosphonic acid tetraethyl ester,
hh) (3-(2-(3-Allyl-4-oxo-6-phenyl-4(3H)-pyrimidinyl))-propylidine)bisphosphonic acid tetraethyl ester, ii) (3-(2-(3-Ethyl-4-oxo-6-phenyl-4(3H)-pyrimidinyl))-propylidine)bisphosphonic acid tetraethyl ester, jj) (3-(2-(3-Propyl-4-oxo-6-phenyl-4(3H)-pyrimidinyl))-propylidine)bisphosphonic acid tetraethyl ester, mm) (3-(2-(3-Methyl-4-oxo-6-(2,3,5-trifluoro-4-piperidinophenyl)-4(3H)-pyrimidinyl)-propylidine)-bis(5,5-dimethyl-2,2'-dioxide-1,3,2-dioxaphosphorinane), oo) 3-(7-Chloro-3-methyl-4(3H)-quinazolinone)-propylidine)bisphosphonic acid tetraethyl ester, pp) 3-(7-Chloro-3-(.alpha.,.alpha.,.alpha.-trifluoro-o-tolyl)-4(3H)-quinazolinone)-propylidine)bisphosphonic acid tetraethyl ester, qq) 3-(7-Chloro-3-(2-fluoro-phenyl)-4(3H)-quinazolinone)-propylidine)bisphosphonic acid tetraethyl ester, and rr) (3-(2-(3-Methyl-4-oxo-6-phenyl-4(3H)-pyrimidinyl))-propylidine)bisphosphonic acid triethyl ester sodium salt.

TABLE 2

| Compound Designation | % Inhibition (10 mg/kg) PO |
| --- | --- |
| p | 60 |
| q | 57 (tested at 1 mg/kg, PO) |
| r | 17 |
| s | 32 |
| t | 7 |
| v | 40 |
| w | 13 |
| x | 6 |
| y | 7 |
| z | 36 |
| aa | 20 |
| bb | 22 |
| cc | 63 |
| ee | 46 |
| gg | 20 |
| hh | 11 |
| ii | 12 |
| jj | 41 |
| mm | 50 |
| oo | 41 |
| pp | 24 |
| qq | 29 |
| rr | 50 |

EXAMPLE 1

(3-(3-Cyano-2,5-dimethyl-pyrazolo(1,5-a)pyrimidin-7-yl)-propylidene)bisphosphonic acid tetraethyl ester (a) and acid salt (b)

Pyrazolo(1,5-a)pyrimidine (3.02 g, 16.2 mmol) was suspended in pyridine (40 ml) at 0° C. and treated with a solution of LiHMDS (1M in THF, 18 mL, 18 mmol). After stirring at 0° C. for 30 min. ethenylidenebis-tetraethyl ester phosphonic acid (hereinafter, ETE phosphonic acid) (4.86 g, 16.2 mmol) was added, the reaction warmed to 22° C., and stirred for 1 hour. It was then poured onto 10% HCl, extracted thrice with methylene chloride, dried with magnesium sulfate and stripped. The sample was purified by chromatography (ethyl acetate, ethyl acetate/acetone 3:1, 2:1, 1:1): 3.97 g (8.16 mmol, 50%). Sample solidified upon standing, m.p. 49°–50° C.

Refluxing the tetraester in concentrated hydrochloric acid for 12 hours and concentrating the solution synthesized the corresponding acid Compound "b" from "a".

EXAMPLE 2

(3-(3-Cyano-5-methyl-2-phenyl-pyrazolo(1,5-a)pyrimidin-7-yl)-propylidene)bisphosphonic acid tetraethyl ester (c)

5,7-dimethyl-2-phenyl-pyrazolo(1,5-a)pyrimidine-3-carbonitrile (621 mg, 2.50 mmol) in pyridine (5.0 mL) at 0° C. was treated with LiHMDS (2.6 mL, 2.6 mmol) and stirred for 30 min. The deep red solution was treated with ETE phosphonic acid (750 mg, 2.50 mmol) in THF (0.5 mL). After stirring for 1 hour at 22° C., the reaction was poured onto 10% HCl. The organics were extracted with methylene chloride, then washed once each with 1N HCl, sodium bicarbonate, and brine, then dried with MgSO₄, and stripped. The sample was purified by chromatography (methylene chloride, methylene chloride/acetone 9:1, then 1:9): 600 mg (1.09 mmol, 49%), m.p. 107° C. (methyl t-butyl ether).

EXAMPLE 3

(3-(3-Bromo-2,5-dimethyl-pyrazolo(1,5-a)pyrimidin-7-yl)-propylidene)bisphosphonic acid tetraethyl ester (d)

3-Bromo-2,5,7-trimethyl-pyrazolo(1,5-a)pyrimidine (460 mg, 1.92 mmol) was dissolved in THF (10 mL) at 0° C. and treated with LiHMDS (2.0 mL, 2.0 mmol). After stirring for 30 min., ETE phosphonic acid (576 mg, 1.92 mmol) in THF (1 mL) was added. After stirring for 1 hour at 22° C., the reaction was poured onto 10% HCl. The organics were extracted with methylene chloride, then washed once each with 1N HCl, sodium bicarbonate, and brine, then dried with MgSO₄, and stripped. The sample was purified by chromatography (ethyl acetate, ethyl acetate/acetone 7:4): 527 mg (0.975 mmol, 51%), an oil.

EXAMPLE 4

(3-(3-Nitro-2,5-dimethyl-pyrazolo(1,5-a)pyrimidin-7-yl)-propylidene)bisphosphonic acid tetraethyl ester (e)

2,5,7-Trimethyl-3-nitro-pyrazolo(1,5-a)pyrimidine (900 mg, 4.36 mmol) was dissolved in pyridine (10 mL) at 0° C., then treated with LiHMDS (4.5 mL, 4.5 mmol). After stirring for 30 min., ETE phosphonic acid (1.31 g, 4.36 mmol) in THF (1 mL) was added. After stirring for 1 hour at 22° C., the reaction was poured onto 10% HCl. The organics were extracted with methylene chloride, then washed once each with 1N HCl, sodium bicarbonate, and brine, then dried with MgSO₄, and stripped. The sample was purified by chromatography (ethyl acetate, ethyl acetate/acetone 7:4): 1.374 g (2.71 mmol, 62%), an oil.

EXAMPLE 5

(3-(2-Benzoyloxy-5-methyl-pyrazolo(1,5-a)pyrimidin-7-yl)-propylidene)bisphosphonic acid tetraethyl ester (f)

A) Cyanoacetohydrazide (9.91 g, 0.10 mmol) and 2,4-pentanedione (10.5 mL, 0.10 mol) were heated for 30 min. in ethanol (20 mL) and acetic acid (0.5 mL). The reaction was cooled to 22° C., then treated with 1N sodium hydroxide (120 mL) and refluxed for 15 min. The stirred hot flask was titrated to neutrality with 12N HCl, then cooled overnight at 0° C. The solid was collected and recrystallized from ethanol: 8.565 g (0.0525 mol, 53%).

5,7-Dimethyl-pyrazolo[1,5-a]pyrimidine-2-ol (3.26 g, 20 mmol) in pyridine (60 mL) at 0° C. was treated with LiHMDS (42 mL, 42 mmol) and stirred for 30 min.

ETE phosphonic acid (6.30 g, 21 mmol) in THF (10 mL) was added and the reaction warmed to 22° C. for 1 hour. The reaction was extracted thrice with 1N sodium hydroxide (20 mL) and these were washed thrice with ethyl acetate. The aqueous fraction was brought to neutrality with 12N HCl, extracted thrice with ethyl acetate, washed with brine, dried with magnesium sulfate, and stripped. The material was used without further purification in the next reaction.

B) The crude pyrazolo[1,5-a]pyrimidine-2-ol (475 mg, 1.02 mmol) in methylene chloride (5 mL) at 0° C. was treated with benzoyl chloride (0.12 mL, 1.02 mmol) and triethyl amine (0.17 mL, 1.2 mmol). After stirring for 1 hour, the reaction was quenched with 1N HCl, extracted thrice with ethyl acetate, then washed with sodium bicarbonate, brine, dried with magnesium sulfate, and stripped. The sample was chromatographed (ethyl acetate, ethyl acetate/acetone 1:1) and the semipure product crystallized upon standing 17%), m.p. 56°–57° C.

EXAMPLE 6

(3-(2-Benzyloxy-5-methyl-pyrazolo(1,5-a)pyrimidin-7-yl)-propylidene)bisphosphonic acid tetraethyl ester (g)

5,7-Dimethyl-pyrazolo[1,5-a]pyrimidine-2-ol (1.63 g, 10 mmol), potassium carbonate (690 mg, 5 mmol), and DMF (6 mL) were heated to 115°–120° C. for 5 min., then treated with benzyl chloride (1.2 mL, 10 mmol). The reaction was stirred for 20 min. at 120° C., then poured onto excess 1N NaOH. The organics were extracted twice with ethyl acetate, then washed with sodium bicarbonate and brine, dried with magnesium sulfate, and stripped. The product crystallized when stripped from hexane, then was recrystallized from hexane with Darco: 539 mg. From the mother liquors an additional 248 mg were recovered: 787 mg (3.10 mmol, 31%).

The benzyl ether (539 mg, 2.1 mmol) in THF (2 mL) at −78° C. was treated with LiHMDS (2.2 mL, 2.2 mmol) and stirred for 30 min. ETE phosphonic acid (630 mg, 2.1 mmol) in THF (1 mL) was added and stirred at 22° C. for 1 hour. The organics were poured onto 10% HCl, extracted thrice with ethyl acetate, washed with sodium bicarbonate and brine, dried with magnesium sulfate, and stripped. The product was isolated by chromatography (ethyl acetate, ethyl acetate/acetone 1:1): 547 mg (0.988 mmol, 47%), an oil.

EXAMPLE 7

(3-(2-Hexyloxy-5-methyl-pyrazolo(1,5-a)pyrimidin-7-yl)-propylidene)bisphosphonic acid tetraethyl ester (h)

5,7-Dimethyl-pyrazolo[1,5-a]pyrimidine-2-ol (1.63 g, 10 mmol), potassium carbonate (690 mg, 5 mmol), and DMF (6 mL) were heated to 115°–120° C. for 5 min., then treated with hexyl bromide (1.5 mL, 10.7 mmol). The reaction was stirred for 20 min. at 120° C., then poured onto excess 1N NaOH. The organics were extracted twice with ethyl acetate, then washed with 1N HCl and brine, dried with magnesium sulfate, and stripped. The product refused to crystallize: 1.876 g (7.6 mmol, 76%).

The crude ether (1.876 g, 7.6 mmol) was dissolved in THF (5 mL), cooled to −78° C., and treated with LiHMDS (7.6 mL, 7.6 mmol). After stirring for 30 min., ETE phosphonic acid (2.27 g, 7.6 mmol) in a trace of THF was added and the reaction was stirred at 22° C. for 1 hour. The organics were poured onto 10% HCl, extracted thrice with ethyl acetate, washed with sodium bicarbonate and brine, dried with magnesium sulfate, and stripped. The product was purified by chromatography (ethyl acetate, ethyl acetate/acetone 1:1): 1.632 g (2.98 mmol, 39%).

EXAMPLE 8

(3-(5-Methyl-2-phenyl-pyrazolo(1,5-a)pyrimidin-7-yl)-propylidene)bisphosphonic acid tetraethyl ester (i)

Pyrazolopyrimidine (1.00 g, 4.5 mmol) dissolved in pyridine (9 mL) was cooled to 0° C. and treated with LiHMDS (4.9 mL, 4.9 mmol) and stirred for 30 min. A solution of ETE phosphonic acid (1.28 g, 4.2 mmol) in THF (4 mL) was added and the solution was stirred for an additional 30 minutes. The reaction mixture was poured into cold 10% HCl and washed three times with methylene chloride. The combined organic layers were washed with 10% HCl, $H_2O$, $NaHCO_3$, NaCl, dried with $MgSO_4$ and stripped. Chromatographed with ethyl acetate followed by 10% acetone/ethyl acetate. The resultant material solidified on standing. The solid was dissolved in ether and precipitated with hexane, m.p. 51°–52° C. Recovered 0.824 g (1.57 mmol, 37%).

EXAMPLE 9

(3-(3-Iodo-5-methyl-2-phenyl-pyrazolo(1,5-a)pyrimidin-7-yl)-propylidene)bisphosphonic acid tetraethyl ester (j)

Compound "i" from Example 8 (0.786 g, 1.5 mmol) dissolved in chloroform (4.8 mL) was treated with N-Iodosuccinimide (0.345 g, 1.54 mmol) and refluxed for 20 min. The solution was cooled and poured onto 2N KOH (6.7 mL). The layers were separated and the chloroform was washed with water, dried with $MgSO_4$ and stripped. Purified by chromatography on silica gel with 2% ethanol/ethyl acetate. The material solidified upon standing, m.p. 81°–82° C. Recovered 0.741 g (1.14 mmol, 76%).

EXAMPLE 10

(3-(3-Chloro-5-methyl-2-phenyl-pyrazolo(1,5-a)pyrimidin-7-yl)-propylidene)bisphosphonic acid tetraethyl ester (k)

Compound "i" from Example 8 (1.490 g, 2.8 mmol) in chloroform (10 mL) was treated with N-Chlorosuccinimide (0.418 g, 3.1 mmol) and refluxed for 30 min. The solution was cooled and poured onto cold 2N KOH (13 mL). Separated and washed the organic layer twice with water and NaCl. Dried with $MgSO_4$ and stripped then chromatographed with 2% ethanol/ethyl acetate. Product solidified upon standing, m.p. 66°–68° C. Recovered 0.763 g (1.37 mmol, 49%).

EXAMPLE 11

(3-(3-Bromo-5-methyl-2-phenyl-pyrazolo(1,5-a)pyrimidin-7-yl)-propylidene)bisphosphonic acid tetraethyl ester (l)

Compound "i" from Example 8 (1.488 g, 2.8 mmol) in chloroform (10 mL) was treated with N-Bromosuccinimide (0.52 g, 2.9 mmol) and the solution was refluxed for 25 min. Cooled and poured onto cold 2N KOH (13 mL) and separated. Washed organic layer twice with water and with brine. Dried with $MgSO_4$ and stripped then chromatographed with 2% ethanol/ethyl acetate. Product solidified upon standing, m.p. 46°–48° C. Recovered 1.47 g (2.44 mmol, 87%).

EXAMPLE 12

(3-(3-Cyano-2,5-dimethyl-pyrazolo(1,5-a)pyrimidin-7-yl)-propylidene)bisphosphonic acid tetramethyl ester (m)

Pyrazolo (1,5-a)pyrimidine (1.25 g, 6.71 mmol) in pyridine (15 mL) at 0° C. was treated with LiHMDS (8.1 mL, 8.1 mmol) and stirred for 30 min. Ethenylidene bis-tetramethyl ester phosphonic acid (1.64 g, 6.71 mmol) was added, the reaction warmed to 22° C. and stirred for 1 hour. The solution was poured onto 10% HCl, extracted thrice with methylene chloride, dried with magnesium sulfate and stripped. The product was recrystallized from ethyl acetate: 1.152 g (2.68 mmol, 40%), m.p. 100°–101° C.

EXAMPLE 13

(3-(3-Cyano-2,5-dimethyl-pyrazolo(1,5-a)pyrimidin-7-yl)-propylidene)bis(5,5-dimethyl-2,2'-dioxide-1,3,2-dioxaphosphorinane) (n)

Pyrazolo (1,5-a)pyrimidine (1.30 g, 6.98 mmol) in pyridine (15 mL) at 0° C. was treated with LiHMDS (7.1 mL, 7.1 mmol) and stirred for 30 min. Solid 1,1' ethenylidene-bis-(5,5-dimethyl-2,2'-dioxide-1,3,2-dioxaphosphorinane) phosphonic acid (2.26 g, 6.98 mmol) was added, the reaction warmed to 22° C., and stirred for 30 min. The reaction was poured onto 10% HCl, extracted thrice with methylene chloride, dried with magnesium sulfate and stripped. The sample was recrystallized from methylene chloride/hexane: 1.743 g (3.41 mmol, 49%), m.p. 258°–259° C.

EXAMPLE 14

(3-(2-(3-Methyl-4-oxo-6-phenyl-4(3H)-pyrimidinyl))-propylidine)bisphosphonic acid tetraethyl ester (p)

To a solution of lithium hexamethyldisilazide (1.0M in THF, 72 ml, 72 mmol) at −78° C. was added dropwise to a solution of 2,3-dimethyl-6-phenyl-pyrimidin-4(3H)-one (13.064 g, 65.16 mmol) in THF (50 ml). After stirring for 30 min. at −78° C., the vinylidene diphosphonate (21.6 g, 72 mmol) was added and the reaction warmed to 22° C. for 1 hour. The reaction was quenched with saturated ammonium chloride, extracted thrice with ethyl acetate, washed twice with brine, dried with magnesium sulfate, and stripped. The material was recrystallized from methyl t-butyl ether: 20.61 g (41.2 mmol, 63%), m.p. 83°–84° C. Additional compounds were obtained by following this same general procedure for the following compounds.

(r) (3-(2-(3-Benzyl-4-oxo-6-phenyl-4(3H)-pyrimidinyl))-propylidine)bisphosphonic acid tetraethyl ester, m.p. 72°–74° C.;

(s) (3-(2-(3-Methyl-4-oxo-6-(3-fluoro-phenyl)-4(3H)-pyrimidinyl)) -propylidine)bisphosphonic acid tetraethyl ester, m.p. 93.5°–95.5° C.;

(t) (3-(2-(3-Allyl-4-oxo-6-phenyl-4(3H)-pyrimidinyl))-propylidine)bisphosphonic acid tetraethyl ester, m.p. 53°–55° C.;

(u) (3-(2-(5-Bromo-3-methyl-4-oxo-6-phenyl-4(3H)-pyrimidinyl)) propylidine)bisphosphonic acid tetraethyl ester, oil, m/e 580, 578 (m+), 443, 441, 293, 291, 288;

(v) (3-(2-(3-Methyl-4-oxo-6-(3-methyl-phenyl)-4(3H)-pyrimidinyl))-propylidine)bisphosphonic acid tetraethyl ester, m.p. 90°–91° C.;

(w) (3-(2-(3-Methyl-4-oxo-6-(3-methoxy-phenyl)-4(3H)-pyrimidinyl))-propylidine) bisphosphonic acid tetraethyl ester, m.p. 65°–66° C.;

(x) (3-(2-(3-Methyl-4-oxo-6-(3-trifluoromethyl-phenyl)-4(3H)-pyrimidinyl))-propylidine)bisphosphonic acid tetraethyl ester, m.p. 77°–79° C.;

(y) (3-(2-(3-Methyl-4-oxo-5 -bromo-6-phenyl-4(3H)-pyrimidinyl))-propylidine)bisphosphonic acid tetraethyl ester, oil, m/e 578 (M+), 441, 291, 288;

(z) (3-(2-(3-Methyl-4-oxo-6-phenyl-4(3H)-pyrimidinyl))-propylidine)bisphosphonic acid tetramethyl ester, mp 106°–108° C.;

(aa) (3-(2-(3-Methyl-4-oxo-6-(4-bromophenyl)-4(3H)-pyrimidinyl))-propylidine)bisphosphonic acid tetraethyl ester, mp 76°–77° C.;

(bb) (3-(2-(3-Methyl-4-oxo-6-(4-methoxyphenyl)-4(3H)-pyrimidinyl))-propylidine)bisphosphonic acid tetraethyl ester, mp 81°–83° C.;

(cc) (3-(2-(3-Methyl-4oxo-6-(4-dimethylaminophenyl)-4-(3H)-pyrimidinyl))-propylidine) bisphosphonic acid tetraethyl ester, mp 92°–94° C.;

(dd) (3-(2-(3-Methyl-4-oxo-6-(3-dimethylaminophenyl)-4-(3H)-pyrimidinyl))-propylidine)bisphosphonic acid tetraethyl ester, mp 79° C.;

(ee) (3-(2-(3-Methyl-4-oxo-6-(4-ethoxyphenyl)-4(3H)-pyrimidinyl))-propylidine)bisphosphonic acid tetraethyl ester, mp 94°–96° C.;

(ff) (3-(2-(3-Methyl-4-oxo-6-(4-methylphenyl)-4(3H)-pyrimidinyl))-propylidine)bisphosphonic acid tetraethyl ester, mp 90°–92° C.;

(gg) (3-(2-(3-Benzyl-4-oxo-6-phenyl-4(3H)-pyrimidinyl))-propylidine)bisphosphonic acid tetraethyl ester, mp 72°–74° C.;

(hh) (3-(2-(3-Allyl-4-oxo-6-phenyl-4(3H)-pyrimidinyl))-propylidine)bisphosphonic acid tetraethyl ester, mp 53°–55° C.;

(ii) (3-(2-(3-Ethyl-4-oxo-6-phenyl-4(3H)-pyrimidinyl))-propylidine)bisphosphonic acid tetraethyl ester, mp 79°–81° C.;

(jj) (3-(2-(3-Propyl-4-oxo-6-phenyl-4(3H)-pyrimidinyl))-propylidine)bisphosphonic acid tetraethyl ester, oil, m/e 528 (M+), 483, 391, 301, 288, 241, 199;

(kk) (3-(2-(3-Benzyloxymethyl-4-oxo-6-phenyl-4(3H)-pyrimidinyl))-propylidine) bisphosphonic acid tetraethyl ester, mp 99.5°–100° C.;

(ll) (3-(2-(3-Methyl-4-oxo-6-phenyl-4(3H)-pyrimidinyl))-propylidine)bis(5,5-dimethyl-2,2'-dioxide-1,3,2-dioxaphosphorinane), mp 244°–245 ° C.; and (mm) (3-(2-(3-Methyl-4-oxo-6-(2,3,5-trifluoro-4-piperidinophenyl)-4(3H)-pyrimidinyl))-propylidine)-bis(5,5-dimethyl-2,2'-dioxide-1,3,2-dioxaphosphorinane), mp 209°–210° C.

EXAMPLE 15

(3-(2-(3-Methyl-4-oxo-6-phenyl-4(3H)-pyrimidinyl))-propylidine)bisphosphonic acid disodium salt (q)

(3-(2-(3-Methyl-4-oxo-6-phenyl-4(3H)-pyrimidinyl))-propylidine)bisphosphonic acid tetraethyl ester (2.29 g, 4.58 mmol) was heated in concentrated hydrochloric acid (20 ml) at reflux for 24 hours, then the solution was stripped to dryness. The residue was suspended in water and the pH was adjusted to 7 with sodium hydroxide. The product was precipitated from the solution with methanol, filtered and air dried: 940 mg (2.17 mmol, 47%), m.p. >300° C.

EXAMPLE 16

(3-(2-(4-Oxo-6-phenyl-4(3H)-pyrimidinyl))-propylidine)bisphosphonic acid tetraethyl ester (nn)

(3-(2-(3-Benzyloxymethyl-4-oxo-6-phenyl-4(3H)-pyrimidinyl))-propylidine)bisphosphonic acid tetraethyl ester, (kk) from Example 15, (1.00 g, 1.65 mmol) was dissolved in ethanol (20 ml), treated with Pearlman's catalyst (500 mg) and ammonium formate (1.0 g), then heated to reflux. After 1.5 hrs, more catalyst (500 mg) and ammonium formate (1.0 g) were added and the reaction continued for 4 more hours. The reaction was cooled to rt, filtered through celite, stripped then chromatographed on silica gel (ethyl acetate, acetone): 138 mg (0.28 mmol, 17%) mp 94°–96° C.

Other compounds were prepared using the same procedure as above and are identified below as follows.

(oo)  3-(7-Chloro-3-methyl-4(3H)-quinazolinone)-propylidine)bisphosphonic acid tetraethyl ester, mp 58°–62° C.;

(pp)  3-(7-Chloro-3-(.alpha.,.alpha.,.alpha.-trifluoro-o-tolyl)-4(3H)-quinazolinone)-propylidine)bisphosphonic acid tetraethyl ester, mp 90°–92° C.; and (qq)  3-(7-Chloro-3-(2-fluoro-phenyl)-4(3H)-quinazolinone)-propylidine)bisphosphonic acid tetraethyl ester, oil, m/e 554 (M+), 534, 509, 417, 301, 288, 267.

EXAMPLE 17

(3-(2-(3-Methyl-4-oxo-6-phenyl-4(3H)-pyrimidinyl))-propylidine)bisphosphonic acid triethyl ester sodium salt (rr)

(3-(2-(3-Methyl-4-oxo-6-phenyl-4(3H)-pyrimidinyl))-propylidine)bisphosphonic acid tetraethyl ester, (p) from Example 14, (1.50 g, 3.0 mmol) was dissolved in methyl ethyl ketone (10 ml), treated with sodium iodide (900 mg, 6 mmol) and heated to reflux overnight. The white precipitate was collected, washed with acetone and ether, then dried in the vacuum oven: 1.337 g (2.70 mmol, 90%) mp>300° C., m/e 517 (M+), 495, 317, 295, 213.

What is claimed:

1. A compound of Formula 1 or pharmaceutically acceptable salts thereof

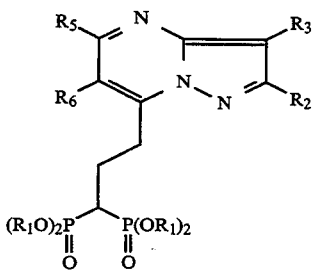

FORMULA 1;

wherein each occurrence of $R_1$ is the same or different and is selected from the group consisting of H, Na, K, $C_1$–$C_6$ alkyl, $CH_2$-phenyl, phenyl (optionally substituted with 1 to 5 $NO_2$, halo, or $C_1$–$C_4$ alkyl), or both $OR_1$ on the same P are taken together along with $CH_2$—$CH_2$, $CH_2$—$CH_2$—$CH_2$, or $CH_2$—$C(CH_3)_2$—$CH_2$ to form a heterocyclic ring having one P, two O and two or three carbon atoms;

$R_2$ is hydrogen, $C_1$–$C_6$ alkyl, benzoyloxy, benzyloxy, $C_1$–$C_6$ alkoxy, phenoxy, $C_3$–$C_7$ cycloalkyl, phenyl (optionally substituted with 1 or 2 phenyls, or 1 to 5 halo, $NO_2$, CN, $CF_3$, $C_1$–$C_{10}$ alkyl, $C_3$–$C_7$ cycloalkyl, $C_1$–$C_6$ alkoxy or $C_1$–$C_6$ alkylthio), 2-, 4- or 5-pyrimidyl (optionally substituted with 1 or 2 phenyls, or 1 to 3 halo, $NO_2$, CN, $CF_3$, $C_1$–$C_{10}$ alkyl, $C_3$–$C_7$ cycloalkyl, $C_1$–$C_6$ alkoxy, or $C_1$–$C_6$ alkylthio), 2-, 3- or 4-pyridyl (optionally substituted with 1 or 2 phenyls, or 1 to 4 halo, $NO_2$, CN, $CF_3$, $C_1$–$C_{10}$ alkyl, $C_3$–$C_7$ cycloalkyl, $C_1$–$C_6$ alkoxy or $C_1$–$C_6$ alkylthio), 1- or 2- naphthalenyl (optionally substituted with 1 or 2 phenyls, or 1 to 7 halo, $NO_2$, CN, $CF_3$, $C_1$–$C_{10}$ alkyl, $C_3$–$C_7$ cycloalkyl, $C_1$–$C_6$ alkoxy or $C_1$–$C_6$ alkylthio);

$R_3$ is H, CN, $CO_2R_1$, $COR_2$, $CON(R_5)_2$, halo, $NO_2$, CN, $CF_3$, $C_1$–$C_{10}$ alkyl, $C_3$–$C_7$ cycloalkyl, or phenyl;

$R_5$ is H, $C_1$–$C_6$ alkyl or $C_3$–$C_7$ cycloalkyl; and $R_6$ is H, halo, or $C_1$–$C_6$ alkyl.

2. The compound of claim 1 wherein said $R_1$ is ethyl.

3. The compound of claim 1 wherein said $R_2$ is methyl, hydrogen or phenyl.

4. The compound of claim 1 wherein said $R_3$ is CN, phenyl, $NO_2$, hydrogen or halo.

5. The compound of claim 1 wherein said $R_5$ is methyl.

6. The compound of claim 1 wherein said $R_6$ is hydrogen.

7. The compound of claim 1 of Formula 1 which is:

a) (3-( 3-Cyano-2,5-dimethyl-pyrazolo(1,5-a)pyrimidin-7-yl)-propylidene)bisphosphonic acid tetraethyl ester, b) (3-(3-Cyano-2,5-dimethyl-pyrazolo(1,5-a)pyrimidin-7-yl)-propylidene)bisphosphonic acid, dipotassium salt, c) (3-(3-Cyano-5-methyl-2-phenyl-pyrazolo(1,5-a)pyrimidin-7-yl)-propylidene)bisphosphonic acid tetraethyl ester, d) (3-(3-Bromo-2,5 -dimethyl-pyrazolo( 1,5-a)pyrimidin-7-yl)-propylidene)bisphosphonic acid tetraethyl ester, e) (3-(3-Nitro-2,5-dimethyl-pyrazolo( 1,5-a)pyrimidin-7-yl)-propylidene)bisphosphonic acid tetraethyl ester, f) (3-(2-Benzoyloxy-5-methyl-pyrazolo(1,5-a)pyrimidin-7-yl)-propylidene)bisphosphonic acid tetraethyl ester, g) (3-(2-Benzyloxy-5-methyl-pyrazolo(1,5-a)pyrimidin-7-yl)-propylidene)bisphosphonic acid tetraethyl ester, h) (3-(2-Hexyloxy-5-methyl-pyrazolo(1,5-a)pyrimidin-7-yl)propylidene)-bisphosphonic acid tetraethyl ester, i) (3-(5-Methyl-2-phenyl-pyrazolo(1,5-a)pyrimidin-7-yl)-propylidene)bisphosphonic acid tetraethyl ester, j) (3-(3-Iodo-5-methyl-2-phenyl-pyrazolo(1,5-a)pyrimidin-7-yl)-propylidene)bisphosphonic acid tetraethyl ester, k) (3-(3-Chloro-5-methyl-2-phenyl-pyrazolo(1,5-a)pyrimidin-7-yl)-propylidene)bisphosphonic acid tetraethyl ester, l) (3-(3-Bromo-5-methyl-2-phenyl-pyrazolo(1,5-a)pyrimidin-7-yl)-propylidene)bisphosphonic acid tetraethyl ester, m) (3-(3-Cyano-2,5-dimethyl-pyrazolo(1,5-a)pyrimidin-7-yl)-propylidene)bisphosphonic acid tetramethyl ester
n) (3-(3-Cyano-2,5-dimethyl-pyrazolo(1,5-a)pyrimidin-7-yl)-propylidene)bis(5,5-dimethyl-2,2'-dioxide-1,3,2-dioxaphosphorinane), or
o) (3-(6-Chloro-3-cyano-2,5-dimethyl-pyrazolo(1,5-a)pyrimidin-7-yl)-propylidene)bisphosphonic acid tetraethyl ester.

8. A method for treating inflammation comprising administering to a patient in need of such treatment an anti-inflammatory effective amount of a compound of claim 1.

9. The method of claim 8 wherein a compound of claim 1 is administered to a patient in need thereof in an anti-inflammatory effective amount of from 0.001 mg to 1.0 gram and is administered orally, intramuscularly, intravenously, transdermally, intra-articularly, subcutaneously, or intraperitoneally.

* * * * *